(12) United States Patent
Kuehn et al.

(10) Patent No.: US 9,717,886 B2
(45) Date of Patent: Aug. 1, 2017

(54) SAFETY CLIP FOR A NEEDLE

(71) Applicant: TELEFLEX MEDICAL INCORPORATED, Research Triangle Park, NC (US)

(72) Inventors: Jeffrey P. Kuehn, Schuylkill Haven, PA (US); Chris Korkuch, Chester Springs, PA (US)

(73) Assignee: TELEFLEX MEDICAL INCORPORATED, Research Triangle, NC (US)

( * ) Notice: Subject to any disclaimer, the term of this patent is extended or adjusted under 35 U.S.C. 154(b) by 14 days.

(21) Appl. No.: 14/205,307

(22) Filed: Mar. 11, 2014

(65) Prior Publication Data
US 2014/0276468 A1 Sep. 18, 2014

Related U.S. Application Data

(60) Provisional application No. 61/778,302, filed on Mar. 12, 2013.

(51) Int. Cl.
*A61M 25/06* (2006.01)

(52) U.S. Cl.
CPC ............... *A61M 25/0618* (2013.01)

(58) Field of Classification Search
CPC ............ A61M 25/0618; A61M 5/3273; A61M 2005/325; A61M 5/326; A61M 2005/3247; A61M 25/0606; A61M 25/0625; A61M 2005/3249; A61M 25/0631; A61M 5/158; A61M 5/3275
See application file for complete search history.

(56) References Cited

U.S. PATENT DOCUMENTS

| 4,160,383 | A | 7/1979 | Rauschenberger |
| 4,616,648 | A | 10/1986 | Simpson |
| 4,798,594 | A | 1/1989 | Hillstead |
| 4,809,679 | A | 3/1989 | Shimonaka et al. |
| 4,857,062 | A | 8/1989 | Russell |
| 4,858,810 | A | 8/1989 | Intlekofer et al. |
| 4,895,346 | A | 1/1990 | Steigerwald |
| 4,895,565 | A | 1/1990 | Hillstead |
| 4,929,241 | A | 5/1990 | Kulli |
| 4,977,897 | A | 12/1990 | Hurwitz |
| 5,009,391 | A | 4/1991 | Steigerwald |
| 5,048,530 | A | 9/1991 | Hurwitz |
| 5,053,017 | A | 10/1991 | Chamuel |
| 5,057,084 | A | 10/1991 | Ensminger et al. |
| 5,084,023 | A | 1/1992 | Lemieux |
| 5,135,504 | A | 8/1992 | McLees |
| 5,176,647 | A | 1/1993 | Knoepfler |
| 5,304,156 | A | 4/1994 | Sylvanowicz et al. |
| 5,312,359 | A | 5/1994 | Wallace |

(Continued)

FOREIGN PATENT DOCUMENTS

| EP | 0386936 A1 | 9/1990 |
| EP | 2433670 A1 | 3/2012 |

(Continued)

*Primary Examiner* — Bhisma Mehta
*Assistant Examiner* — Brandy S Lee
(74) *Attorney, Agent, or Firm* — Baker Hostetler LLP

(57) ABSTRACT

A safety clip that securely and reversibly attaches to an assembly of a catheter and needle is disclosed. The safety clip securely enshrouding a needle tip of the needle following use of the needle.

21 Claims, 21 Drawing Sheets

(56) References Cited

U.S. PATENT DOCUMENTS

| | | |
|---|---|---|
| 5,318,541 A | 6/1994 | Viera et al. |
| 5,325,746 A | 7/1994 | Anderson |
| 5,350,363 A | 9/1994 | Goode et al. |
| 5,389,100 A | 2/1995 | Bacich et al. |
| 5,405,323 A | 4/1995 | Rogers et al. |
| 5,409,464 A | 4/1995 | Villalobos |
| 5,562,619 A | 10/1996 | Mirarchi et al. |
| 5,611,792 A | 3/1997 | Gustafsson |
| 5,613,663 A | 3/1997 | Schmidt et al. |
| 5,637,096 A | 6/1997 | Yoon |
| 5,704,914 A | 1/1998 | Stocking et al. |
| 5,766,135 A | 6/1998 | Terwilliger |
| 5,769,795 A | 6/1998 | Terwilliger |
| 5,858,007 A | 1/1999 | Fagan et al. |
| 6,050,976 A | 4/2000 | Thorne et al. |
| 6,053,870 A | 4/2000 | Fulton, III |
| 6,117,108 A | 9/2000 | Woehr et al. |
| 6,197,001 B1 | 3/2001 | Wilson et al. |
| 6,228,060 B1 | 5/2001 | Howell |
| 6,287,278 B1 | 9/2001 | Woehr et al. |
| 6,287,280 B1 | 9/2001 | Lampropoulos et al. |
| 6,299,602 B1 | 10/2001 | Miller et al. |
| 6,413,250 B1 | 7/2002 | Smith |
| 6,443,929 B1 | 9/2002 | Kuracina et al. |
| 6,506,181 B2 | 1/2003 | Meng et al. |
| 6,551,282 B1 | 4/2003 | Exline et al. |
| 6,565,542 B2 | 5/2003 | Kumar et al. |
| 6,595,955 B2 | 7/2003 | Ferguson et al. |
| 6,602,240 B2 | 8/2003 | Hermann et al. |
| 6,610,016 B1 | 8/2003 | Violante et al. |
| 6,616,630 B1 | 9/2003 | Woehr et al. |
| 6,626,869 B1 | 9/2003 | Bint |
| 6,629,959 B2 | 10/2003 | Kuracina et al. |
| 6,652,486 B2 | 11/2003 | Bialecki et al. |
| 6,652,490 B2 | 11/2003 | Howell |
| 6,699,221 B2 | 3/2004 | Vaillancourt |
| 6,709,419 B2 | 3/2004 | Woehr |
| 6,719,726 B2 | 4/2004 | Meng et al. |
| 6,749,588 B1 | 6/2004 | Howell et al. |
| 6,796,962 B2 | 9/2004 | Ferguson et al. |
| 6,860,856 B2 | 3/2005 | Ward et al. |
| 6,860,865 B1 | 3/2005 | Feldgiebel |
| 6,902,546 B2 | 6/2005 | Ferguson |
| 6,972,002 B2 | 12/2005 | Thorne |
| 6,984,213 B2 | 1/2006 | Horner et al. |
| 6,986,749 B2 | 1/2006 | Wollschlager |
| 7,004,927 B2 | 2/2006 | Ferguson et al. |
| 7,008,402 B2 | 3/2006 | Ferguson et al. |
| 7,008,404 B2 | 3/2006 | Nakajima |
| 7,044,936 B2 | 5/2006 | Harding et al. |
| 7,179,244 B2 | 2/2007 | Smith et al. |
| 7,186,239 B2 | 3/2007 | Woehr |
| 7,226,434 B2 | 6/2007 | Carlyon et al. |
| 7,247,148 B2 | 7/2007 | Murashita |
| 7,264,613 B2 | 9/2007 | Woehr et al. |
| 7,291,128 B2 | 11/2007 | Rossi et al. |
| 7,291,130 B2 | 11/2007 | McGurk |
| 7,341,573 B2 | 3/2008 | Ferguson et al. |
| 7,347,838 B2 | 3/2008 | Kulli |
| 7,357,784 B2 | 4/2008 | Ferguson |
| 7,374,554 B2 | 5/2008 | Menzi et al. |
| 7,413,562 B2 | 8/2008 | Ferguson et al. |
| 7,458,954 B2 | 12/2008 | Ferguson et al. |
| 7,476,244 B2 | 1/2009 | Buzzard et al. |
| 7,534,227 B2 | 5/2009 | Kulli |
| 7,544,184 B2 | 6/2009 | Cope et al. |
| 7,556,617 B2 | 7/2009 | Voorhees, Jr. et al. |
| 7,597,681 B2 | 10/2009 | Sutton et al. |
| 7,604,616 B2 | 10/2009 | Thoresen et al. |
| 7,608,057 B2 | 10/2009 | Woehr et al. |
| 7,611,485 B2 | 11/2009 | Ferguson |
| 7,611,499 B2 | 11/2009 | Woehr et al. |
| 7,618,395 B2 | 11/2009 | Ferguson |
| 7,625,360 B2 | 12/2009 | Woehr et al. |
| 7,632,243 B2 | 12/2009 | Bialecki et al. |
| 7,635,352 B2 | 12/2009 | Adams |
| 7,637,893 B2 | 12/2009 | Christensen et al. |
| 7,651,476 B2 | 1/2010 | Kohler |
| 7,670,317 B2 | 3/2010 | Cindrich et al. |
| 7,682,331 B2 | 3/2010 | Carrez et al. |
| 7,682,344 B2 | 3/2010 | Barrelle |
| 7,691,088 B2 | 4/2010 | Howell |
| 7,713,243 B2 | 5/2010 | Hillman |
| 7,731,687 B2 | 6/2010 | Menzi et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,340 B2 | 6/2010 | Harding et al. |
| 7,744,568 B2 | 6/2010 | Douglas et al. |
| 7,753,877 B2 | 7/2010 | Bialecki et al. |
| 7,762,993 B2 | 7/2010 | Perez |
| 7,806,849 B2 | 10/2010 | Woehr |
| 7,828,774 B2 | 11/2010 | Harding et al. |
| 7,833,199 B2 | 11/2010 | Franer et al. |
| 7,938,805 B2 | 5/2011 | Harding et al. |
| 7,951,121 B2 | 5/2011 | Weaver et al. |
| 7,967,829 B2 | 6/2011 | Gunderson et al. |
| 7,972,313 B2 | 7/2011 | Woehr et al. |
| 7,976,502 B2 | 7/2011 | Baid |
| 7,988,664 B2 | 8/2011 | Fiser et al. |
| 8,038,647 B2 | 10/2011 | Harding et al. |
| 8,048,039 B2 | 11/2011 | Carlyon et al. |
| 8,052,647 B2 | 11/2011 | Raulerson et al. |
| 8,066,675 B2 | 11/2011 | Cindrich et al. |
| 8,162,881 B2 | 4/2012 | Lilley, Jr. et al. |
| 8,162,939 B2 | 4/2012 | Shizuka |
| 8,177,772 B2 | 5/2012 | Christensen et al. |
| 8,211,070 B2 | 7/2012 | Woehr et al. |
| 8,235,971 B2 | 8/2012 | Christensen et al. |
| 8,251,950 B2 | 8/2012 | Albert et al. |
| 8,257,315 B2 | 9/2012 | Franer et al. |
| 8,273,056 B2 | 9/2012 | Kuracina et al. |
| 8,292,852 B2 | 10/2012 | Mulholland et al. |
| 8,298,181 B2 | 10/2012 | Perez |
| 8,328,762 B2 | 12/2012 | Woehr et al. |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,348,893 B2 | 1/2013 | Carlyon |
| 8,369,935 B2 | 2/2013 | Ryan |
| 8,382,721 B2 | 2/2013 | Woehr et al. |
| 8,403,886 B2 | 3/2013 | Bialecki et al. |
| 8,449,530 B2 | 5/2013 | Bacher et al. |
| 8,460,247 B2 | 6/2013 | Woehr et al. |
| 8,480,627 B2 | 7/2013 | Christiansen |
| 8,486,024 B2 | 7/2013 | Steube |
| 8,500,696 B2 | 8/2013 | Kobayashi et al. |
| 8,506,528 B2 | 8/2013 | Fiser et al. |
| 8,523,819 B2 | 9/2013 | Abe et al. |
| 8,535,271 B2 | 9/2013 | Fuchs et al. |
| 8,540,728 B2 | 9/2013 | Woehr et al. |
| 8,647,301 B2 | 2/2014 | Bialecki et al. |
| 9,011,351 B2 | 4/2015 | Hoshinouchi |
| 9,126,017 B2 | 9/2015 | Albert et al. |
| 2002/0026151 A1 | 2/2002 | Miller et al. |
| 2004/0106891 A1 | 6/2004 | Langan et al. |
| 2004/0127855 A1 | 7/2004 | Core |
| 2005/0075609 A1* | 4/2005 | Latona ............... A61M 5/3273 604/164.08 |
| 2005/0096592 A1* | 5/2005 | Carlyon ............. A61M 5/3273 604/110 |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038187 A1 | 2/2007 | Albert et al. |
| 2007/0073221 A1 | 3/2007 | Bialecki et al. |
| 2007/0073270 A1 | 3/2007 | Christensen et al. |
| 2007/0156093 A1 | 7/2007 | Woehr |
| 2007/0270753 A1 | 11/2007 | Kulli |
| 2008/0065015 A1* | 3/2008 | Fiser ................ A61M 25/0618 604/110 |
| 2008/0300574 A1 | 12/2008 | Belson et al. |
| 2009/0082732 A1 | 3/2009 | Hillman |
| 2009/0143738 A1 | 6/2009 | Hendriksen et al. |

(56) References Cited

U.S. PATENT DOCUMENTS

| | | |
|---|---|---|
| 2009/0163861 A1 | 6/2009 | Carlyon |
| 2009/0163871 A1 | 6/2009 | Burkholz et al. |
| 2009/0177114 A1 | 7/2009 | Chin et al. |
| 2009/0247986 A1 | 10/2009 | Rioux et al. |
| 2009/0247994 A1 | 10/2009 | Bacher et al. |
| 2009/0299291 A1 | 12/2009 | Baid |
| 2009/0312711 A1 | 12/2009 | Brimhall |
| 2010/0042076 A1 | 2/2010 | McCarthy et al. |
| 2010/0087755 A1 | 4/2010 | Boezaart |
| 2010/0094310 A1 | 4/2010 | Warring et al. |
| 2010/0168756 A1 | 7/2010 | Dorn et al. |
| 2010/0191188 A1 | 7/2010 | Harding et al. |
| 2010/0191189 A1 | 7/2010 | Harding et al. |
| 2010/0191224 A1 | 7/2010 | Butcher |
| 2010/0204654 A1 | 8/2010 | Mulholland et al. |
| 2010/0249707 A1 | 9/2010 | Woehr et al. |
| 2011/0009849 A1 | 1/2011 | Christensen et al. |
| 2011/0213307 A1 | 9/2011 | Kawai et al. |
| 2011/0282280 A1 | 11/2011 | Fiser et al. |
| 2011/0282285 A1 | 11/2011 | Blanchard et al. |
| 2011/0288482 A1 | 11/2011 | Farrell et al. |
| 2011/0319825 A1 | 12/2011 | Goral et al. |
| 2011/0319838 A1 | 12/2011 | Goral et al. |
| 2012/0059247 A1 | 3/2012 | Speeg et al. |
| 2012/0078200 A1* | 3/2012 | Woehr ............... A61M 5/158 604/263 |
| 2012/0089094 A1 | 4/2012 | Franer et al. |
| 2012/0095404 A1 | 4/2012 | Massengale et al. |
| 2012/0116248 A1 | 5/2012 | McWeeney et al. |
| 2012/0123339 A1 | 5/2012 | Abe et al. |
| 2012/0172806 A1 | 7/2012 | Woehr et al. |
| 2012/0179104 A1 | 7/2012 | Woehr et al. |
| 2012/0184910 A1 | 7/2012 | Woehr |
| 2012/0197200 A1 | 8/2012 | Belson |
| 2012/0203181 A1 | 8/2012 | Woehr et al. |
| 2012/0215171 A1 | 8/2012 | Christiansen |
| 2012/0220942 A1 | 8/2012 | Hall et al. |
| 2012/0220956 A1 | 8/2012 | Kuracina et al. |
| 2012/0271235 A1 | 10/2012 | Fuchs et al. |
| 2012/0271247 A1 | 10/2012 | Weaver et al. |
| 2012/0277679 A1 | 11/2012 | Steube |
| 2012/0283553 A1 | 11/2012 | Cully et al. |
| 2013/0006101 A1 | 1/2013 | McHugo et al. |
| 2013/0030372 A1 | 1/2013 | Franer et al. |
| 2013/0046315 A1 | 2/2013 | Woehr et al. |

FOREIGN PATENT DOCUMENTS

| | | |
|---|---|---|
| JP | 2010512803 A | 4/2010 |
| JP | 2013529111 A | 7/2013 |
| WO | WO2007003874 A1 | 1/2007 |
| WO | WO2007006055 A2 | 1/2007 |
| WO | WO2010078151 A1 | 7/2010 |
| WO | WO2011143621 A1 | 11/2011 |
| WO | WO2010012023 A1 | 2/2012 |
| WO | WO2015023358 A1 | 2/2015 |

* cited by examiner

SAFETY CLIP FOR A NEEDLE

CROSS REFERENCE TO RELATED APPLICATION

This application claims the benefit of U.S. Provisional Application No. 61/778,302, filed on Mar. 12, 2013, the disclosure of which is hereby incorporated by reference in its entirety.

FIELD OF THE DISCLOSURE

The present disclosure relates to safety devices that slide on a needle, clip securely on the needle, and shield the tip of the needle.

BACKGROUND OF THE DISCLOSURE

In clinical practice, injuries from needles are common, in particular because of blood and infective agents that contaminate the used needle. These injuries, which are occupational hazards of the medical profession, have resulted in inadvertent transmission of infective agents such as hepatitis C and human immunodeficiency virus. Sharps collection boxes, gloves and various safety practices are used to mitigate physical injuries arising from used needles, and to prevent infections from the needles. Also, devices that use active retraction, encased needles, shields, or self-blunting have been used (see, e.g., Elder et al (2006) Occupational Med. 56:566-574; Wilburn (2004) Online J. Issues Nurs. 9:5). However, the presently available safety devices for protecting against injuries and infections resulting from needles are not completely fail-safe. The present disclosure addresses this unmet need, by providing a new safety clip for a needle.

SUMMARY OF THE DISCLOSURE

This application describes a clip that securely and removably attaches to a needle of a catheter assembly. The clip securely enshrouds a needle tip following use of the needle.

The clip can be configured to secure to a hub of a medical device, and is also configured to secure to a needle that is inserted at least partially through the hub. When in a secure mounted state, the clip is securely mounted on the hub, and when the clip is in a detached state, it is not mounted on the hub. The clip includes at least one tab that is configured to be placed into a corresponding at least one tab placement portion in the hub. The clip also includes a spring arm that presses against the needle in the mounted state, and that also presses against the needle in the detached state. The force of the spring arm against the needle is greater in the mounted state than in the detached state. The clip also includes a proximal aperture that stabilizes the needle and allows reversible movement of the needle through the proximal aperture of the clip in a direction parallel to the needle longitudinal axis in said mounted state. The proximal aperture prevents movement of the needle in a direction that is parallel to the longitudinal axis of the needle in the detached state. The clip also includes a distal aperture that allows reversible movement of the needle in the direction of the longitudinal axis of needle in said mounted state.

In addition, the clip can include a central aperture that allows reversible movement of the needle parallel to the longitudinal axis of needle in said mounted state, where the central aperture does not constrain needle movement relative to the clip in the direction parallel to needle longitudinal axis in said mounted state. Moreover, the proximal aperture does not exert stick-and-slip friction against needle in the mounted state, but does exert stick-and-slip friction against needle in the detached state.

In some implementations, the central aperture also does not exert stick-and-slip friction against needle in the mounted state. Moreover, the at least one tab can be male member and the at least one tab receipt portion of the hub can be a female member. The hub can be a catheter hub. The medical device can be a catheter and the needle can be a syringe needle. Between 50% and 100% of the mass of the clip can be exterior to the hub. The clip can be in an assembled combination with a hub or a catheter. The clip can be in an assembled combination with a needle and a hub, or with a needle and a catheter.

In some implementations, the needle can be inserted at least partially through the hub and at least 90% of the mass of the clip is not housed within or enclosed by the hub or the catheter. The clip includes a first aperture that stabilizes the needle and allows reversible movement of the clip along the longitudinal axis of needle in the mounted state, and a second aperture that allows reversible movement of the clip along the longitudinal axis of needle in said mounted state.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

BRIEF DESCRIPTIONS OF THE DRAWINGS

FIGS. 1A, 1B, 1C, and 1D illustrate a non-limiting relationship between a clip, a hub, and a needle. In particular, FIG. 1A illustrates a clip assembled with a hub and a needle in a mounted state. FIG. 1B illustrates a clip assembled only with the needle, where the hub is removed in a detached state. FIG. 1C illustrates a blow-up of a region where the needle passes through an aperture of the clip when the clip is attached to the hub. FIG. 1D illustrates blow-up of region where the needle passes through aperture of tilted clip body when the clip is removed from the hub.

Figure 7A:
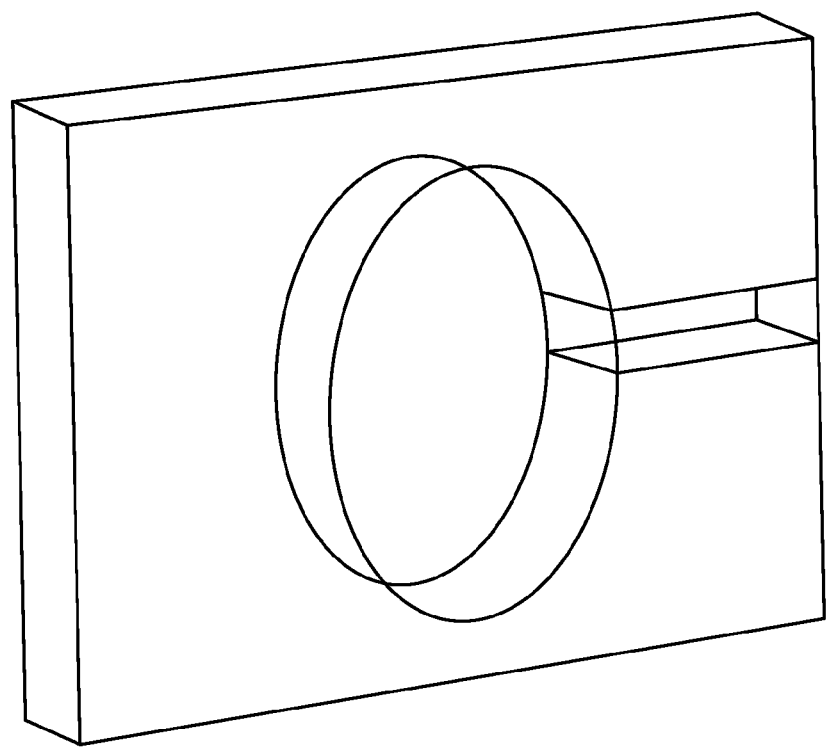
Figure 7B:
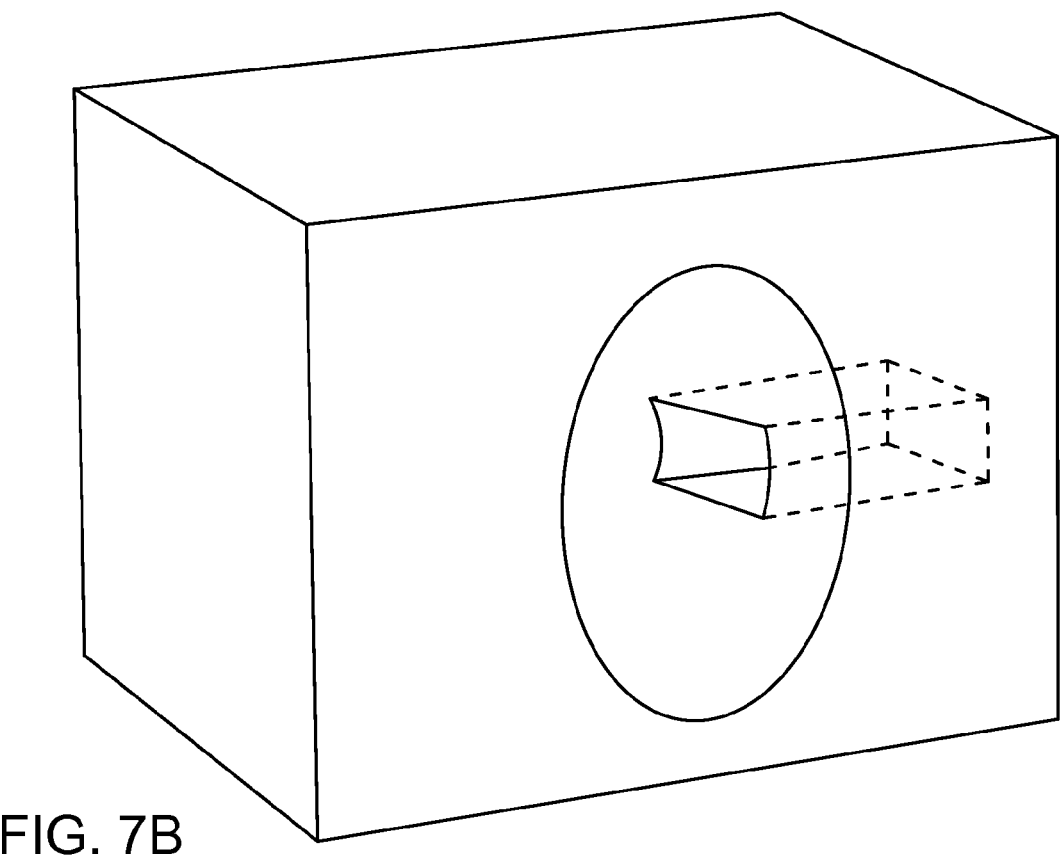
Figure 7C:
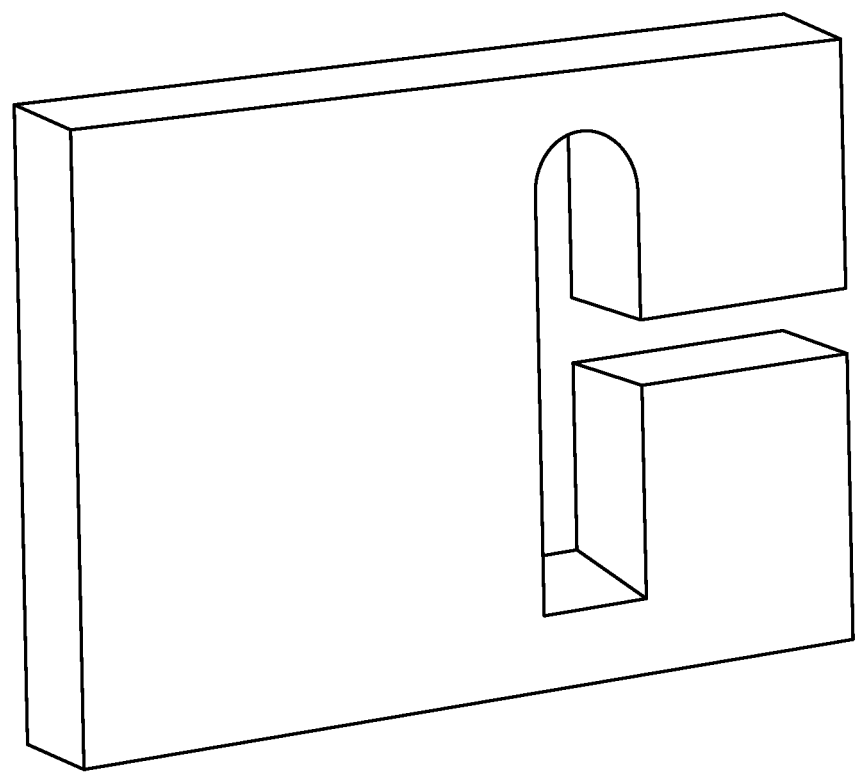

FIGS. 7A, 7B, and 7C illustrate a device where an aperture, a groove, or a tube contains a break. FIG. 7A illustrates the aperture with a break. FIG. 7B illustrates the tube with a break. FIG. 7C illustrates the groove with a break.

Figure 8A:
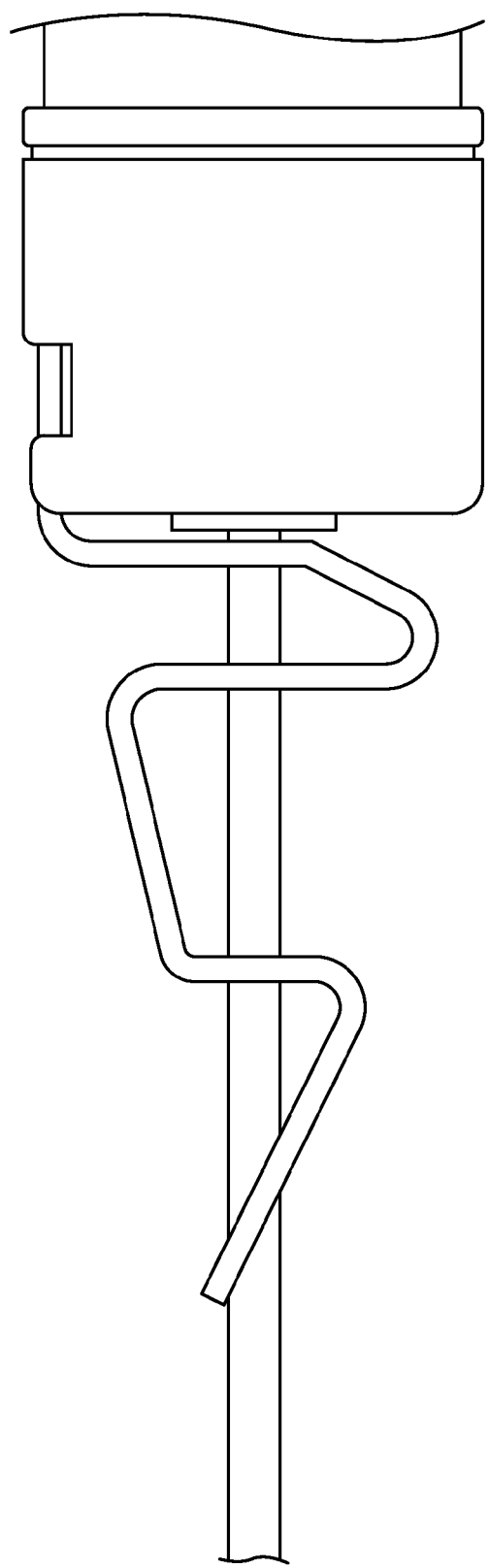
Figure 8B:
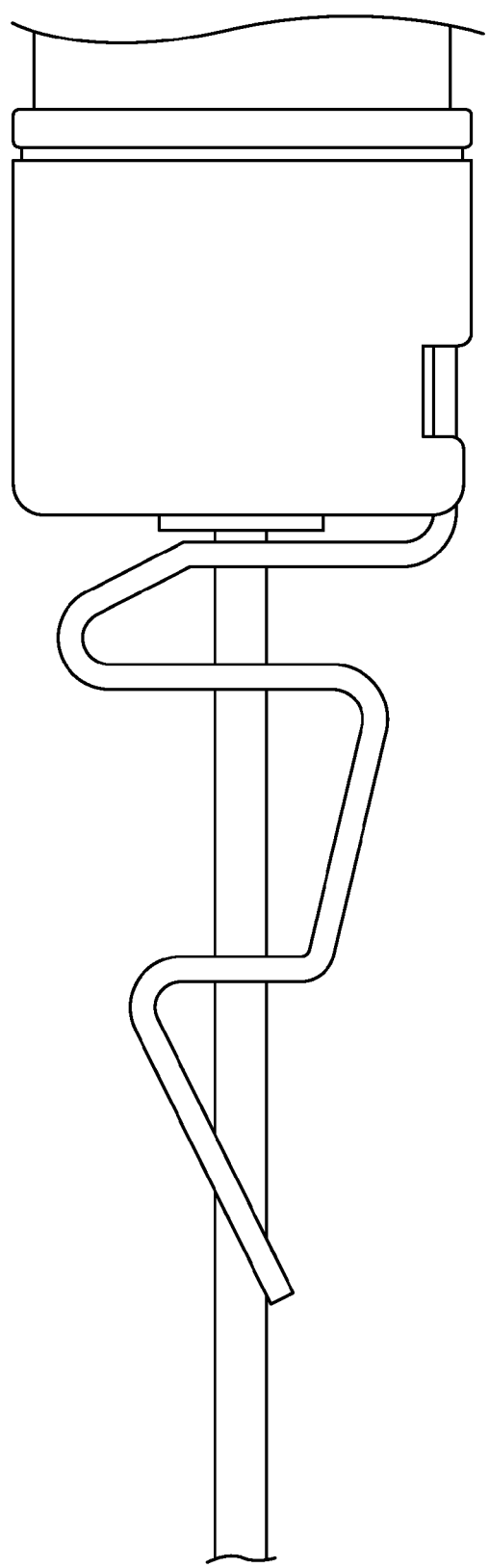

FIGS. 8A and 8B illustrate a side view of a first implementation of a clip in a mounted state with a hub. In particular, FIG. 8A illustrates a side view of the first implementation of the clip in the mounted state with the hub being right-side up. FIG. 8B illustrates a side view of the first implementation of the clip in the mounted state with the hub being upside down.

Figure 9A:
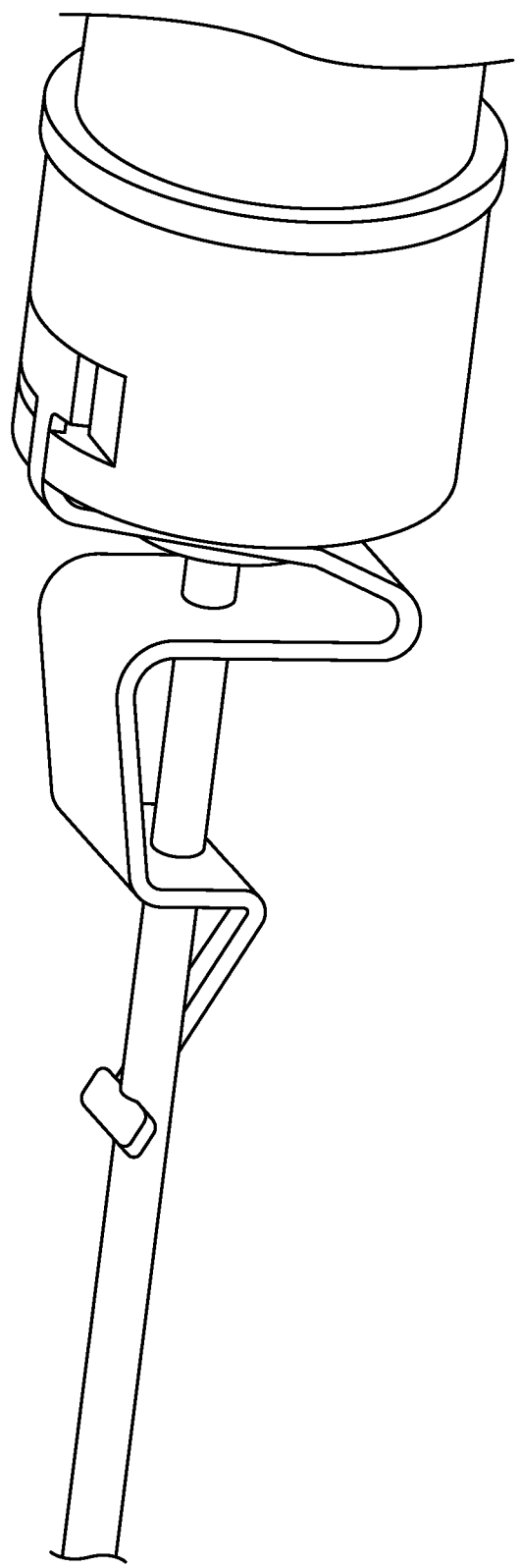
Figure 9B:
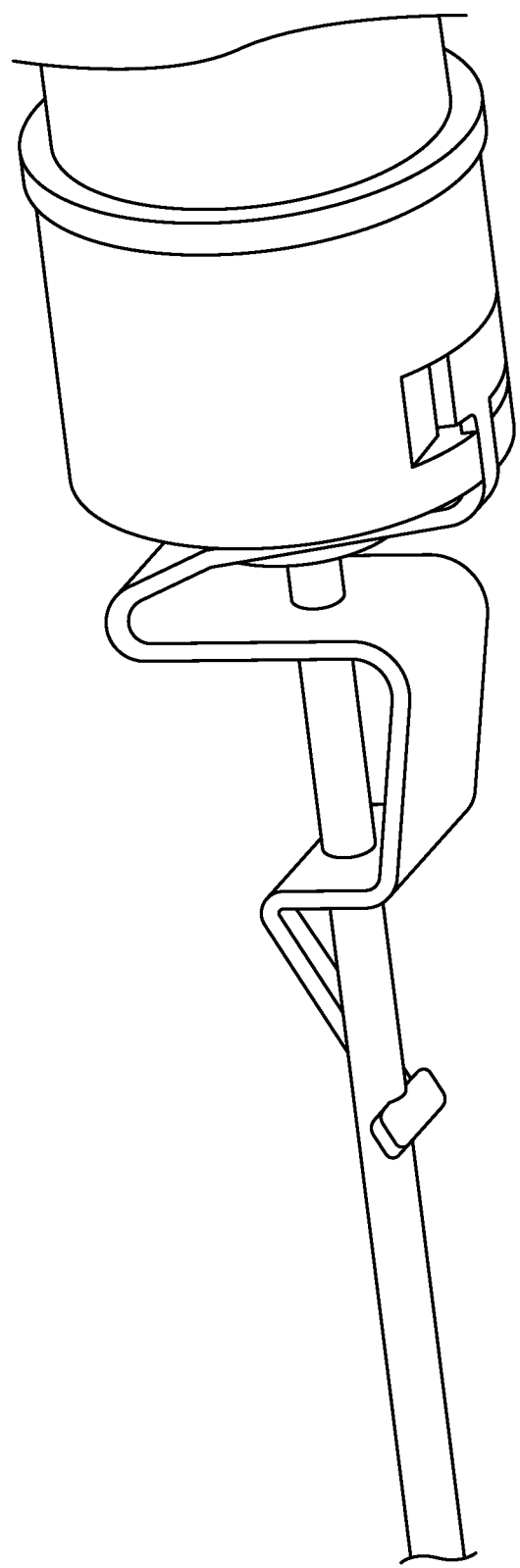

FIGS. 9A and 9B illustrate a three-dimensional perspective view of the first implementation of the clip in the mounted state with the hub. In particular, FIG. 9A illustrates a three-dimensional perspective view of the first implementation of the clip in the mounted state with the hub being right-side up. FIG. 9B illustrates a three-dimensional perspective view of the first implementation of the clip in the mounted state with the hub being upside down.

Figure 10A:
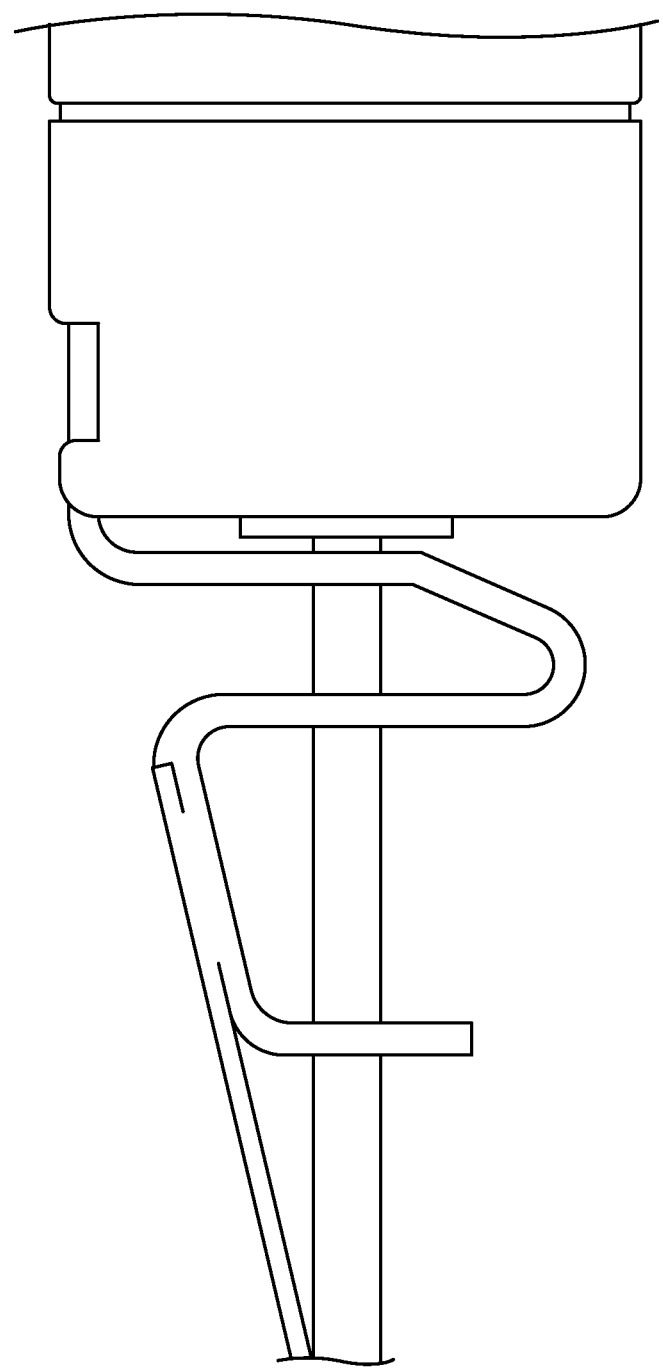
Figure 10B:
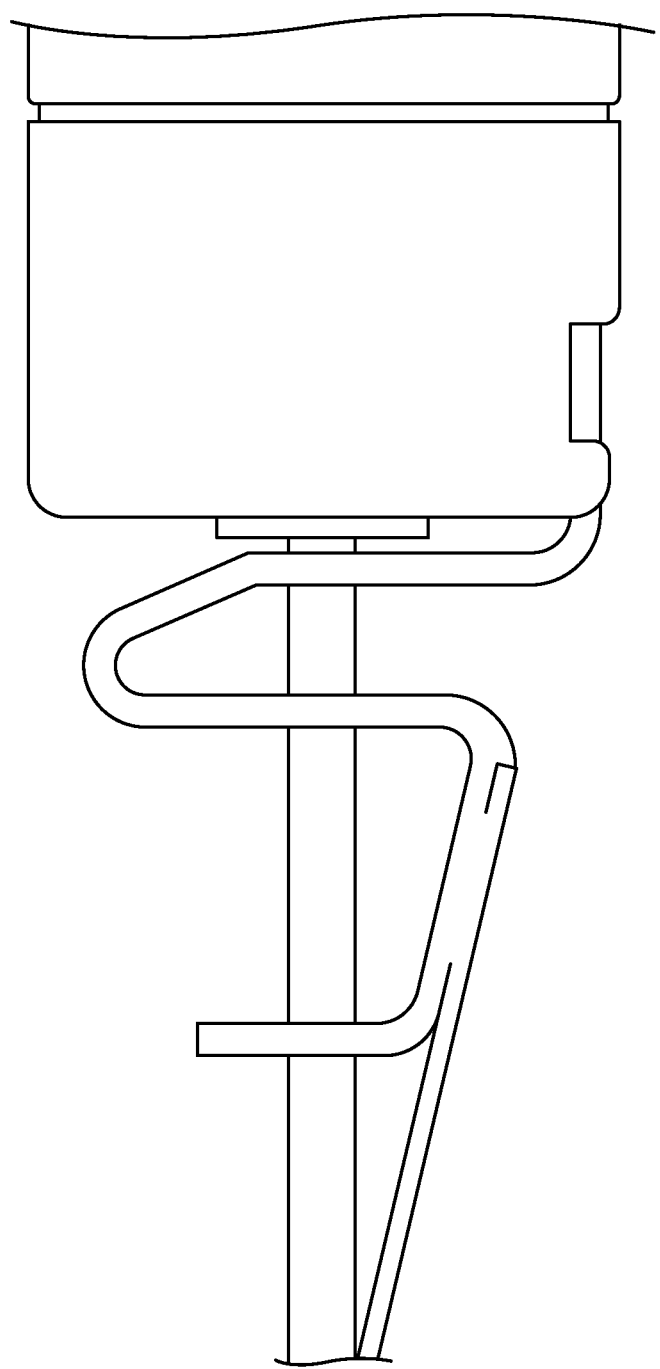

FIGS. 10A and 10B illustrate a side view of a second implementation of a clip in a mounted state with a hub. In particular, FIG. 10A illustrates a side view of the second implementation of the clip in the mounted state with the hub being right-side up. FIG. 10B illustrates a side view of the second implementation of the clip in the mounted state with the hub being upside down.

Figure 11A:
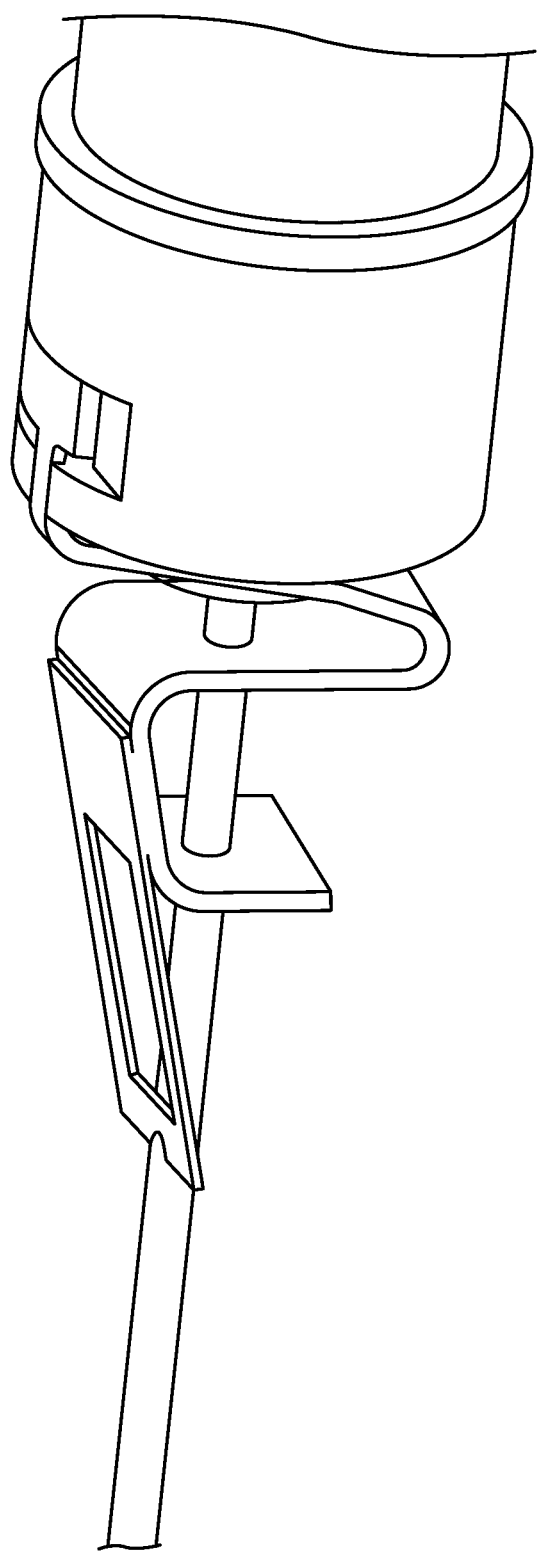
Figure 11B:
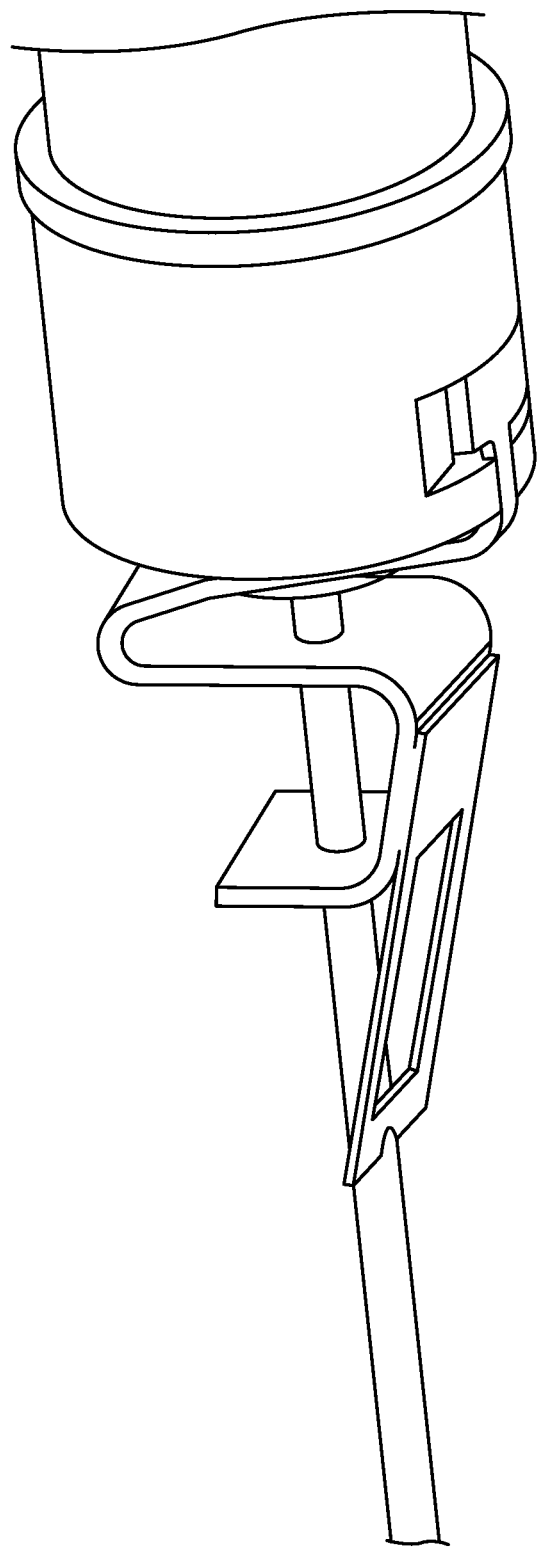

FIGS. 11A and 11B illustrate a three-dimensional perspective view of the second implementation of the clip in the mounted state with the hub. In particular, FIG. 11A illustrates a three-dimensional perspective view of the second implementation of the clip in the mounted state with the hub being right-side up. FIG. 11B illustrates a three-dimensional perspective view of the second implementation of the clip in the mounted state with the hub being upside down.

Figure 12A:
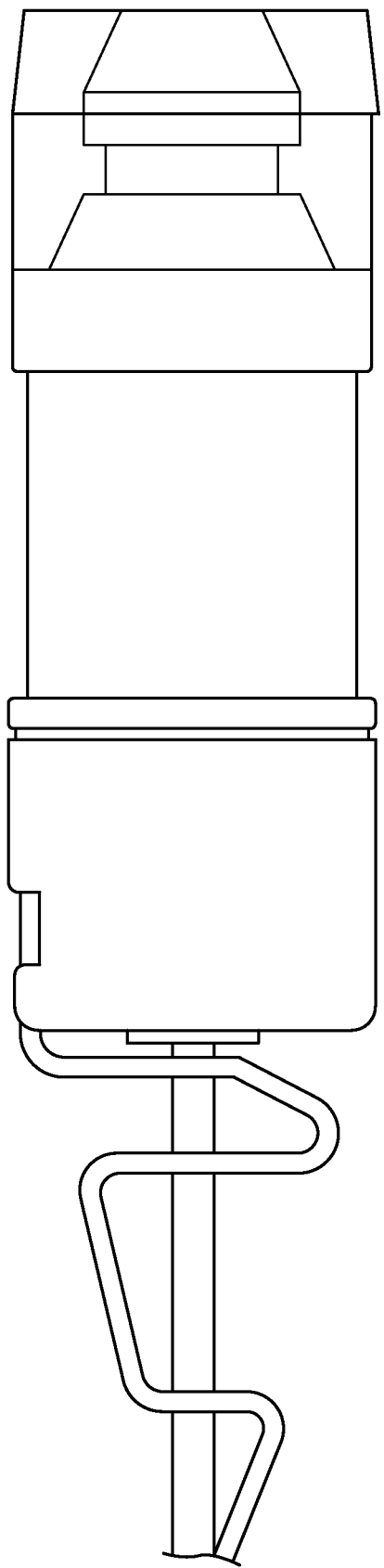
Figure 12B:
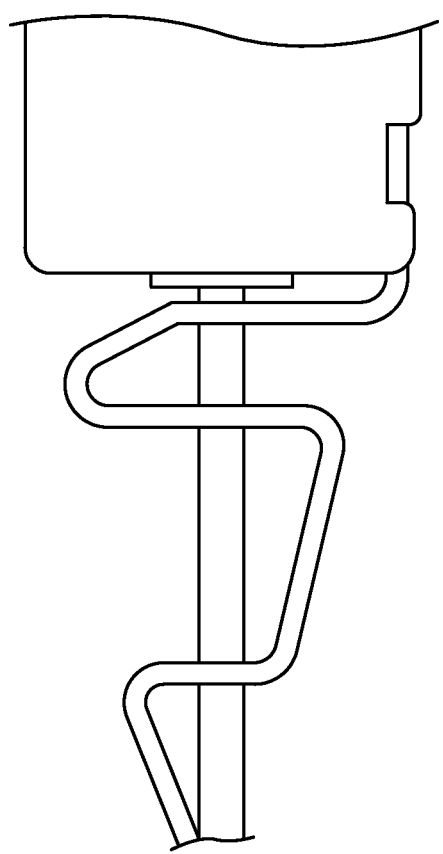

FIGS. 12A and 12B illustrate a side view of a third implementation of a clip in a mounted state with a hub. In particular, FIG. 12A illustrates a side view of the third implementation of the clip in the mounted state with the hub being right-side up. FIG. 12B illustrates a side view of the third implementation of the clip in the mounted state with the hub being upside down.

Figure 13A:
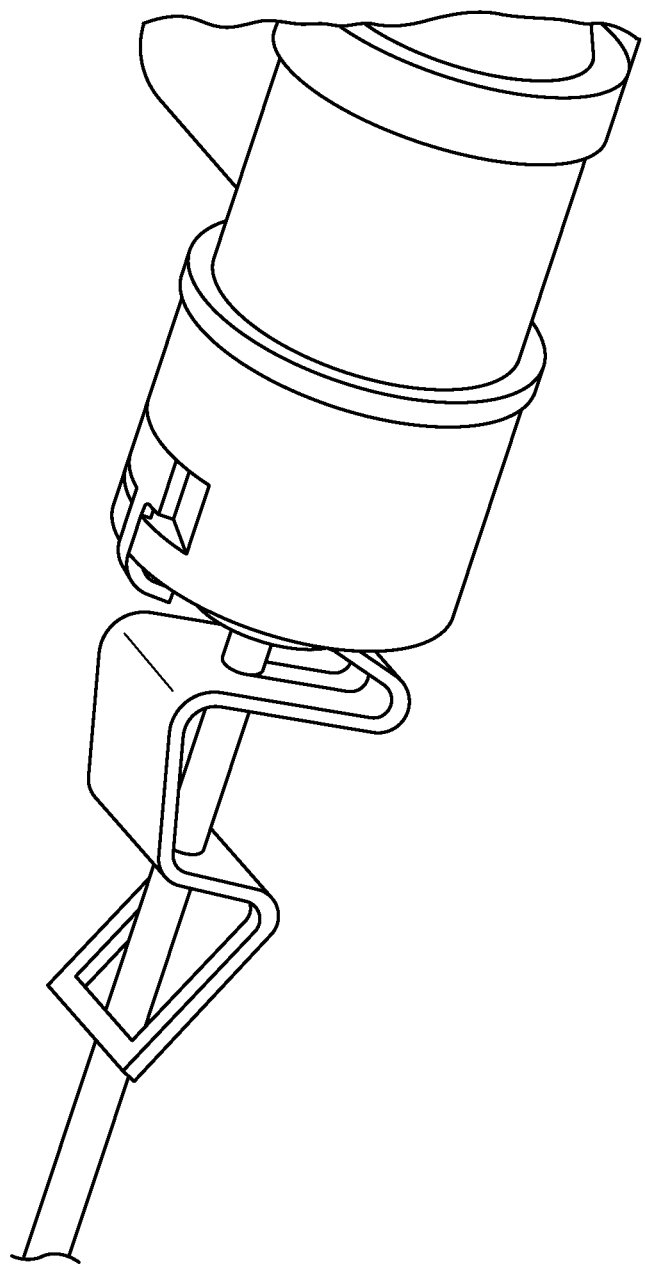
Figure 13B:
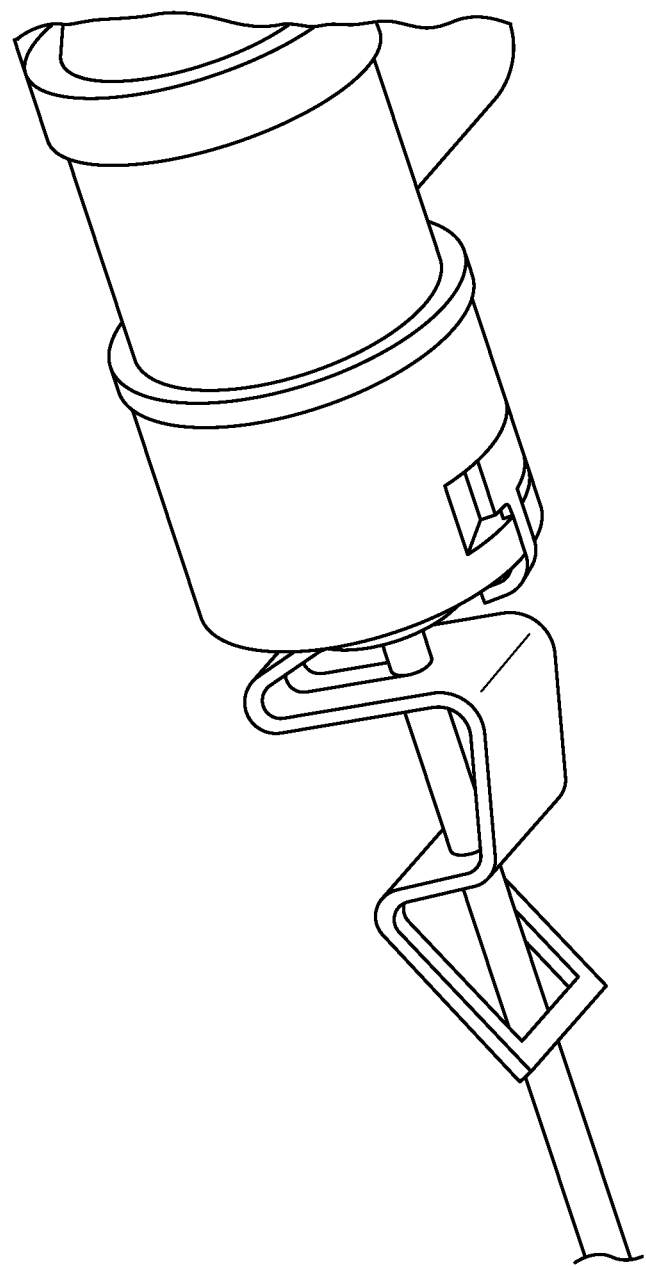

FIGS. 13A and 13B illustrate a three-dimensional perspective view of the third implementation of the clip in the mounted state with the hub. In particular, FIG. 13A illustrates a three-dimensional perspective view of the third implementation of the clip in the mounted state with the hub being right-side up. FIG. 13B illustrates a three-dimensional perspective view of the third implementation of the clip in the mounted state with the hub being upside down.

DETAILED DESCRIPTION OF THE DISCLOSURE

In the description and claims below, various terms may be used for which the following definitions will apply:
Proximal and Distal In the context of a medical device, such as an assembly having a longitudinal aspect, such as an assembly of a sheath and dilator, "proximal" refers generally to the end of the assembly that is closest to the physician while "distal" refers generally to the end that is inserted into the patient. Where the terms "proximal-to-distal movement" or "proximal-to-distal force" are used, these terms can refer to the context where the device is being used with the patient, and also in an abstract context, where a physician and patient are not present.
French Size Diameters of catheters, cannulas, tubes, and the like, can be labeled by French size. This disclosure provides a tube with a French size that is, to provide non-limiting examples, 3 Fr (1 mm; 0.039 inches), 4 Fr (1.35 mm; 0.053 inches), 5 Fr (1.67 mm; 0.066 inches), 6 Fr (2 mm; 0.079 inches), 7 Fr (2.3 mm; 0.092 inches), etc. The corresponding diameters in millimeters and inches are shown in parenthesis. The French system has uniform increments between gauge sizes (⅓ of a millimeter) (Iserson K V (1987) J.-F.-B. Charrière: the man behind the "French" gauge. J. Emerg. Med. 5:545-548). Systems for measuring the outside diameter and inside diameter of lumens of catheters, needles, and the like have been described (see, e.g., Ahn, et al. (2002) Anesth. Analg. 95:1125). French size can refer to an inside diameter or to an outside diameter (see, e.g., U.S. Pat. No. 7,641,645 issued to Schur, which is hereby incorporated by reference).
Couplers and Locks In some embodiments, the present disclosure provides a coupler or lock, such as a Luer lock or unisex Storz type coupler (see, e.g., U.S. Pat. No. 4,602,654 of Stehling et al). Locking tabs are also provided (see, e.g., U.S. Pat. No. 5,885,217 issued to Gisselberg et al). Also provided is a coupler with one or more radially-oriented protrusions that fit into one or more radially-oriented grooves (see, e.g., U.S. Pat. No. 6,336,914 of Gillespie). A locking collar can also be provided (see, e.g., U.S. 2005/0090779 of Osypka). Also provided is a coupler, with a proximal-to-distal (axially-oriented) pin or pins that fit into one or more slots (see, e.g., U.S. 2009/0143739 of Nardeo et al). Further provided is a threaded coupler (see, e.g., U.S. Pat. No. 7,422,571 of Schweikert et al). Each of the above patents and published patent applications are hereby incorporated herein by reference, in their entirety. In some embodiments, what is encompassed is a valve, or a medical device that includes a valve and that excludes any one of the above couplers. A coupler can couple a first hub to a second hub. For example, a first hub that is a catheter hub and a second hub that is a needle hub can be coupled. The first hub can be a catheter hub and the second hub can be a sheath hub.

Exclusionary Embodiments

The present disclosure encompasses medical devices, safety clips, and related methods of use. In every implementation disclosed below, the clip is not fully enclosed by a cowl or housing. In particular, 10% or less of the clip is enclosed by or within a cowl, housing, or hub. The clip of the present disclosure can also be used in combination with a catheter.

Methods and equipment are available to the skilled artisan for measuring structures, properties and functions of medical devices, such as catheters. The following references disclose methods and equipment for measuring, for example, tensile strength, force at break, elastic behavior, plastic behavior, microscopy for detecting microbial colonies or biofilms residing on the surface of catheters, or microbiological assays for measuring influence of antimicrobials. See, e.g., Aslam and Darouiche (2010) Infect. Control Hosp. Epidemiol. 31:1124-1129; Hachem et al (2009) Antimicrobial Agents Chemotherapy 53:5145-5149; Venkatesh et al (2009) J. Medical Microbiol. 58:936-944, which are hereby incorporated herein by reference. Methods and equipment for measuring tensile strength, elongation at break, and other properties of medical devices are also available. See, e.g., U.S. Pat. No. 6,039,755 issued to Edwin et al, and U.S. Pat. No. 7,803,395 issued to Datta et al, which are incorporated herein by reference. Above a limiting stress, called the elastic limit, some of the strain is permanent. In going beyond the elastic limit, a solid can either fracture suddenly or deform in a permanent way (see, e.g., Ashby M F, Jones D R H (2012) Engineering Materials 1, 4$^{th}$ ed., Elsevier, New York, pp. 115-133).

Coatings

The present disclosure provides, without limitation, coatings that comprise sulfobetaine, or carboxybetaine, hydrogels, polyurethane, polyester, polyethylene, polyamide, diblock polymers, layered coatings, interpenetrating polymer networks, or mixtures thereof. See, e.g., U.S. Pat. No. 7,879,444 issued to Jiang et al; U.S. 2009/0259015 of Jiang and Chen; U.S. 2009/0155335 of O'Shaughnessey et al; U.S. 2009/0156460 of Jiang et al; U.S. 2010/0145286 of Zhang et al; 2011/0097277 of Jiang et al; and U.S. 2010/0152708 of Li et al, each of which is individually incorporated herein by reference in its entirety.

Metals

The present disclosure provides metals, metal composites, plastics, ceramics, and other materials for manufacturing a clip. Also provided are materials, such as ribbons or leafs that are springs or have spring-like qualities. The skilled artisan is familiar with the relevant materials and techniques, including techniques for assessing torsion, flexibility, resiliency, pressure, friction, springiness, and so on. See, e.g., Walsh (2000) Handbook of Machining and Metalworking Calculations. McGraw-Hill; Nelson and Schneider (2000) Applied Manufacturing Process Planning: With Emphasis on Metal Forming and Machining. Prentice Hall; Strong (2007) Fundamentals of Composites Manufacturing: Materials, Methods and Applications, Society of Manufacturing Engineers; Bover and Gall (1984) Metals Handbook, Asm. Int'l The clip can be made substantially of one material. Alternatively, different parts of clip, for example, head, body, tail, and spring arm, can be made of different materials.

Aperture

An "aperture" encompasses any hole that is large enough to allow passage of a syringe needle. The syringe needle can have a diameter at a point along its substantially tubular portion that is in the range of 0.1-0.2 mm, 0.2-0.4 mm, 0.4-0.6 mm, 0.6-0.8 mm, 0.8-1.0 mm, 1.0-1.2 mm, 1.2-1.4 mm, 1.4-1.6 mm, 1.6-1.8 mm, 1.8-2.0 mm, and the like.

The present disclosure provides a clip that has a spring arm, where the spring arm is configured to be more flexible, or more resilient, or springier, than other parts of the clip. In this embodiment, the spring arm that is configured to be more flexible can be formed of a different material (e.g., different type of metal) than other parts of the clip. Alternatively, or in addition, the spring arm can be configured to be more flexible by taking the form of a strip, ribbon, or plank that is thinner than other parts of the clip.

FIG. 1 illustrates a non-limiting relationship between an implementation of a clip, a hub, and a needle. FIG. 1A shows the clip assembled with the hub and the needle. A needle 2 includes a needle tip 1. The needle 2 is received within the hub 3 and a clip 4 is proximal of the hub 3. FIG. 1B illustrates the clip 11 assembled only with the needle 13 when the hub 10 is removed. In this examples, the clip 11 is secured about the needle tip 12 protecting the practitioner from the needle tip. Action of the spring arm compels tilting of the clip 11, where tilting results in gripping of the clip to the needle 13. Gripping can result from an internal edge of an aperture, which is sharp, being tilted so that it "digs" into the longitudinal body of the needle. The clip 11 is triggered after the tip 12 of the needle 13 is proximal of the distal face of the clip 11, and the clip 11 has detached from the hub 10, which detaches the hub 10 from the clip 11. When the hub 10 is freed, the spring arm becomes larger and relatively uncompressed, resulting in tilting of the clip 11, misalignment of the needle tip 12 and the most distal aperture of the clip 11, and detachment of the clip 11 and the hub 10.

Figure 1A:
Figure 1B:
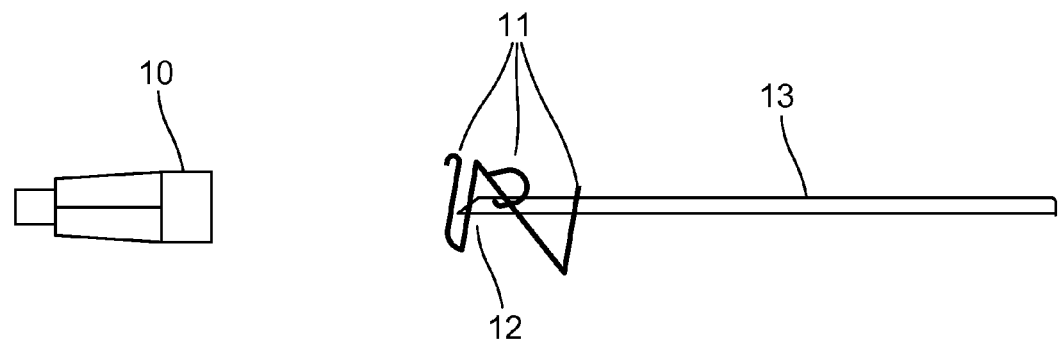
Figure 1C:
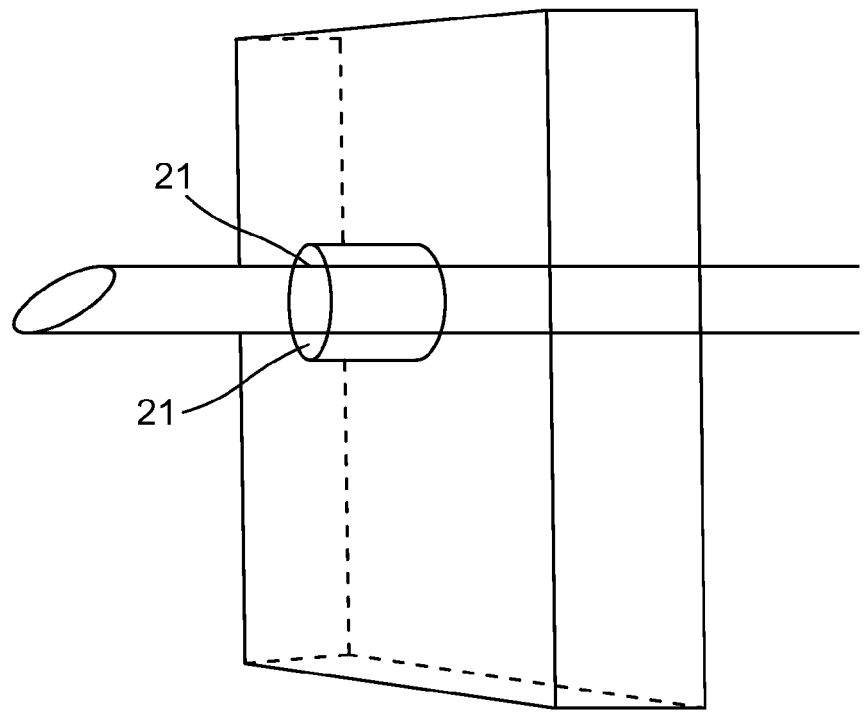
Figure 1D:
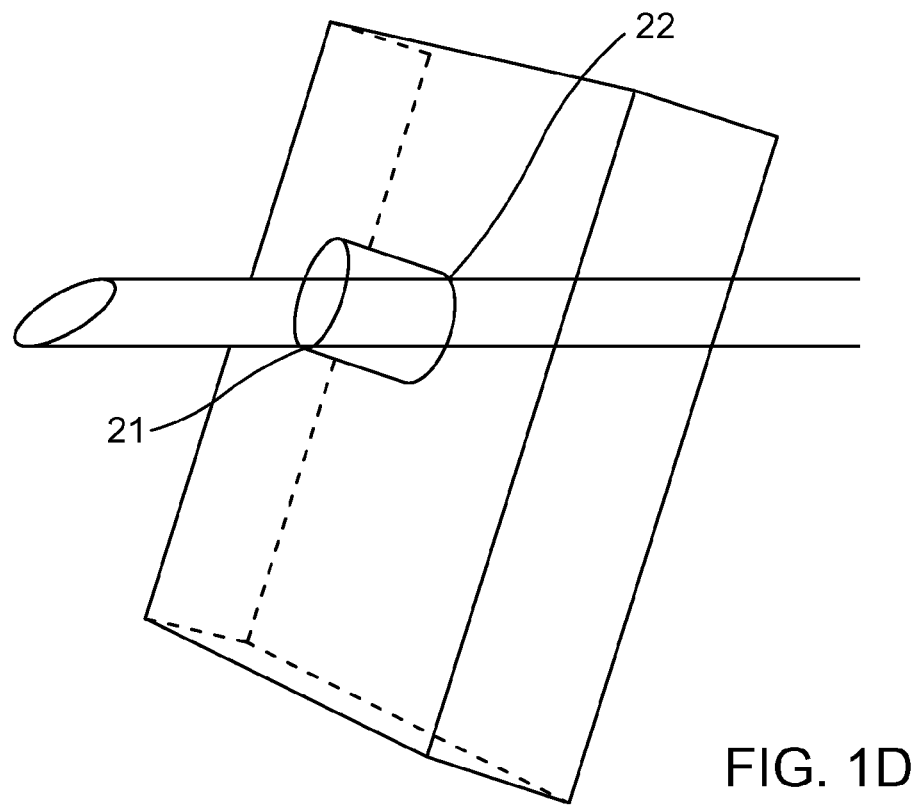

FIG. 1C illustrates a blow-up of a region where the needle passes through an aperture 21 of the clip with little friction. FIG. 1D illustrates a blow-up of a region where the needle passes through an aperture of a tilted clip, where friction caused by sharp edges 22 of the clip dig into needle. The increased friction in FIG. D can be of the stick-and-slip variety. Various types of friction have been described (see, e.g., Ashby M F, Jones D R H (2012) Engineering Materials 1, 4$^{th}$ ed., Elsevier, New York, pp. 115-133).

Figure 2:
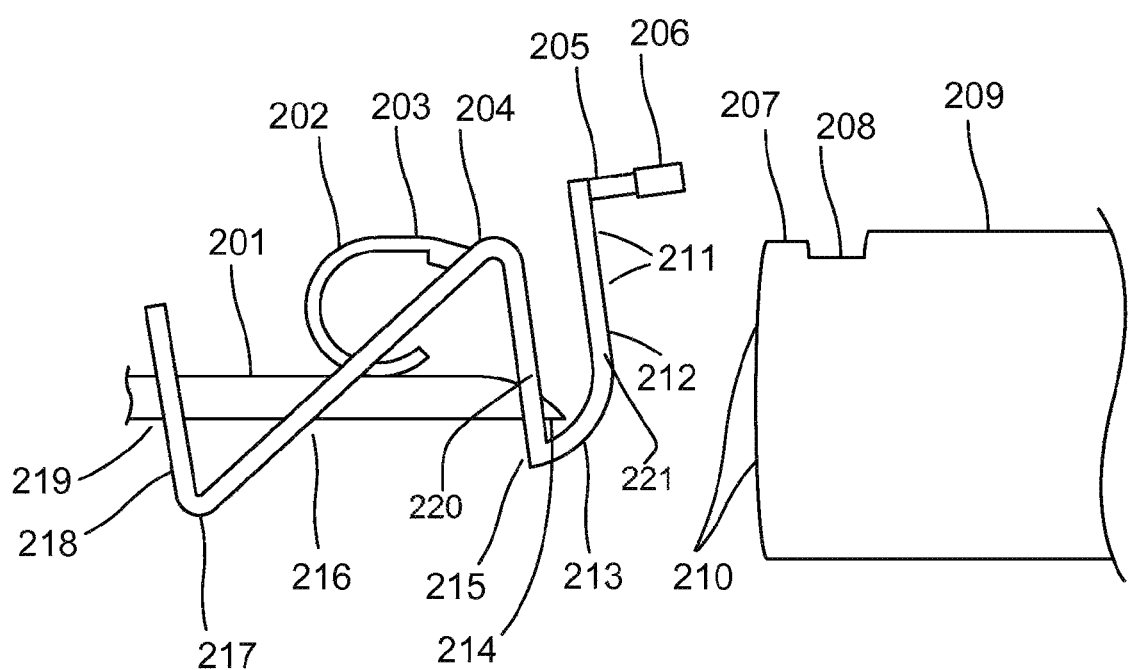
FIG. 2 illustrates a side view of a combination of an implementation of a clip and a needle tip in a detached state.

FIG. 2 illustrates a side view of a combination of an implementation of a clip and a needle tip in a detached state. A needle or cannula 201 with a needle tip 214 is partially within a clip. The clip includes a spring arm 202 in extended conformation where the clip is detached from the hub 209. The spring arm 202 includes a spring arm proximal portion 203. The clip further includes a clip second bend 204, a clip narrow tab 205, and a clip broad tab 206. The hub 209 includes a hub narrow notch 207 that is hidden behind annular region of hub that is adjacent to hub face 210, and a hub broad notch 208. The hub face 210 faces proximally and is located at the proximal end of the hub 209, and is not visible in FIG. 2. The clip face 211 faces distally and is located at the distal end of the clip, and is not visible in FIG. 2. The distal end of the clip includes a first distal wall 220 and a second distal wall 221 connected at a third clip bend 215. A clip third aperture 212 is also not visible in FIG. 2. A clip head 213 is between a clip second bend 204 and the clip narrow tab 205. The clip also includes a clip body 216 that is between a clip head 213 and a clip tail 218. A clip second aperture in the clip body is also not visible in FIG. 2. The clip also includes the clip first bend 217 and a clip tail 218 includes a clip first aperture 219. The clip first aperture 219 is not visible in FIG. 2.

As shown in FIG. 2, for example, the spring arm 202 is C-shaped. The C-shape is non-limiting, and other shapes can be stepped, blocked, jagged, amorphous, and so on. Spring arm 202 extends from clip head 213, and extends proximally in direction away from needle tip, where the length of proximal extension provides leverage. The distance of the proximal extension of spring arm can be, for example, 0.1-0.2 mm, 0.2-0.3 mm, 0.3-0.4 mm, 0.4-0.5 mm, 0.5-0.6 mm, 0.6-0.7 mm, 0.7-0.8 mm, 0.8-0.9 mm, 1.0-1.1-mm, 1.1-1.2 mm, 1.2-1.5 mm, 1.5-2.0 mm, 2.0-2.2 mm, 2.2-2.5 mm, 2.5-3.0 mm, 3.0-3.2 mm, 3.2-3.5 mm, 3.5-4.0 mm, 4.0-4.2 mm, 4.2-4.5 mm, 4.5-5.0 mm, 5.0-10.0 mm, 10-20 mm, 20-30 mm, and the like, or any combination thereof, such as the range of 5.0 millimeters to 2.0 centimeters.

Figure 3:
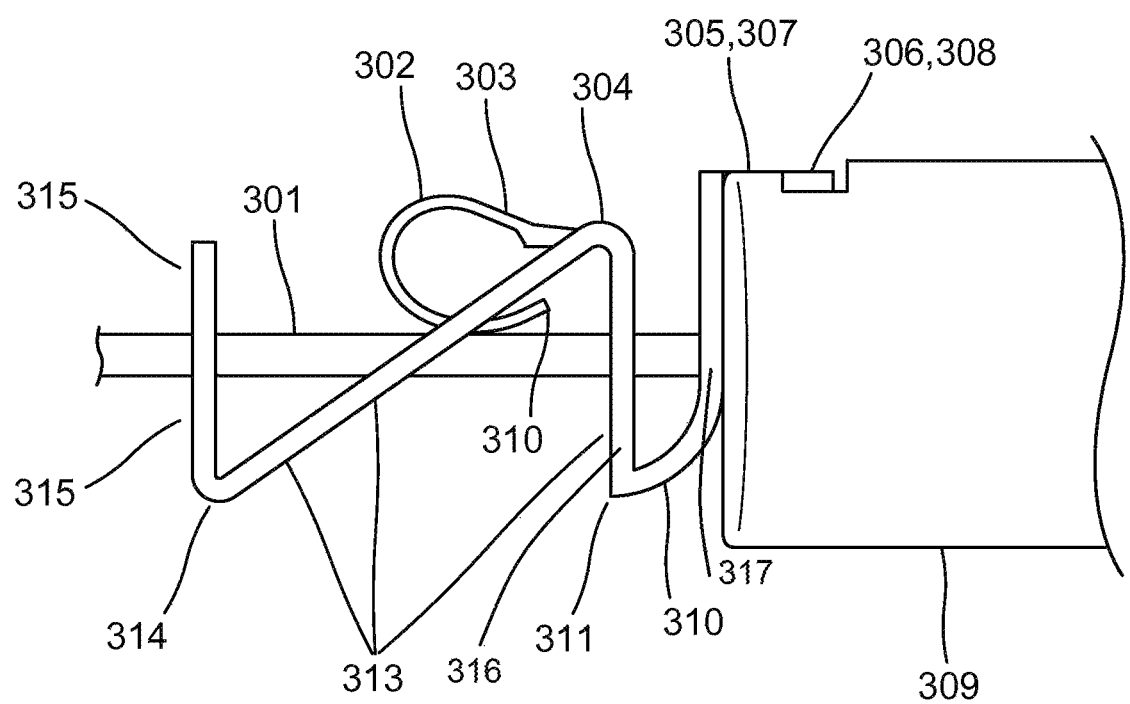
FIG. 3 illustrates a side view of a combination of an implementation of a clip, a needle tip, and a hub in a mounted state.

FIG. 3 illustrates a side view of a combination of an implementation of a clip, a needle tip, and a hub in a mounted state. A needle or cannula 301 includes a spring arm 302 in a compressed conformation. When the clip is attached to the hub 309, the spring arm 302 is compressed and presses firmly on the needle 301, and when the clip is detached from hub 309, the spring arm 302 expands somewhat, and continues to press down on needle 301 with less force. The spring arm 302 includes a spring arm proximal position 303. The clip includes a clip second bend 304, a clip narrow tab 305 that resides in a hub narrow notch 307. The clip includes a clip wide tab 306 that resides in a hub broad notch 308. The clip also includes a clip head 310 that is between the clip second bend 304 and the clip narrow tab 305. The clip also includes a clip third bend 311 connecting a first distal wall 316 and a second distal wall 317, a spring arm distal portion 310, a clip body 313, a clip first bend 314, and a clip tail 315.

Figure 4:
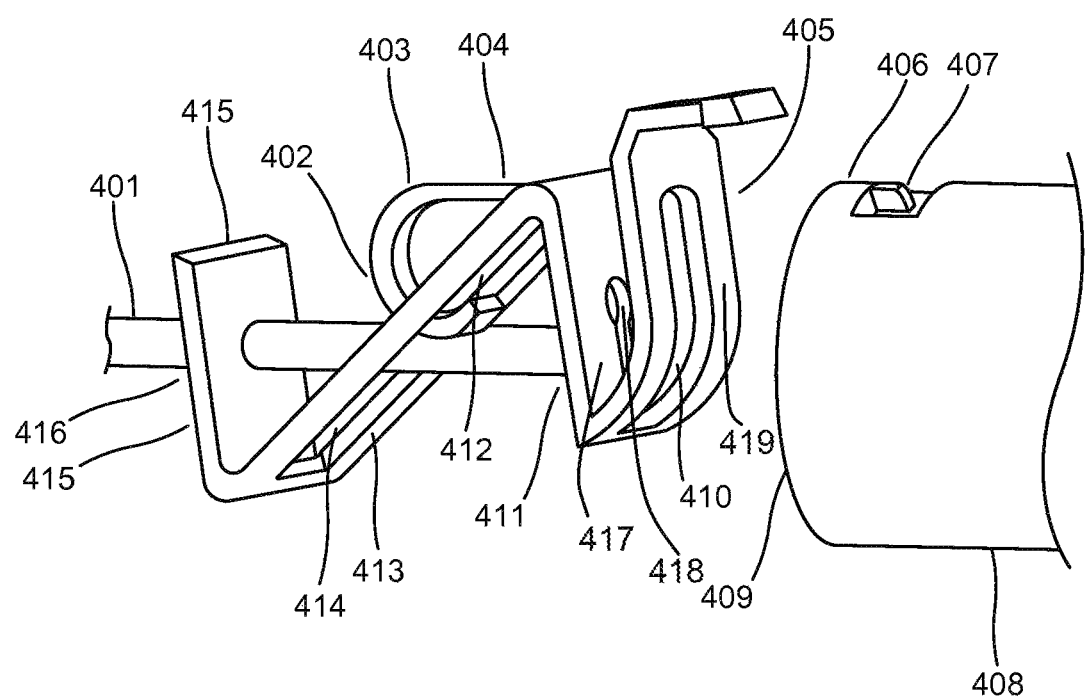
FIG. 4 illustrates a perspective view of a combination of an implementation of a clip and a needle tip showing a clip face.

FIG. 4 illustrates a prospective view of a combination of an implementation of a clip and a needle tip, showing a clip face 405. A needle or cannula 401 is at least partially within a clip. The clip includes a spring arm with a spring arm distal portion 402, a spring arm central portion 403, and a spring arm proximal portion 404. When mounted, the clip face 405 contacts the hub face 409. The clip face 405 and the hub face 409 need not be planar, but can be sinusoidal, have a washboard surface, have corresponding pimples on the clip face 405 and dimples on the hub face 409, and so on. Preferably, the clip face 405 and the hub face 409 contact one another, thereby helping to stabilize assembled combination of clip and hub 408. The hub 408 also includes a hub narrow notch 406 and a hub broad notch 407. The clip includes a distal portion having a first distal wall 417 defining a first distal aperture 418, a second distal wall 419 defining a clip third aperture 410, a clip body 411, and a clip second aperture 412. The clip also includes a clip body 413, a clip second aperture 414 in its proximal portion, a clip tail 415, and a clip first aperture 416 (not shown). Preferably, the clip face 405 and the hub face 409 have a mating geometry.

Figure 5:
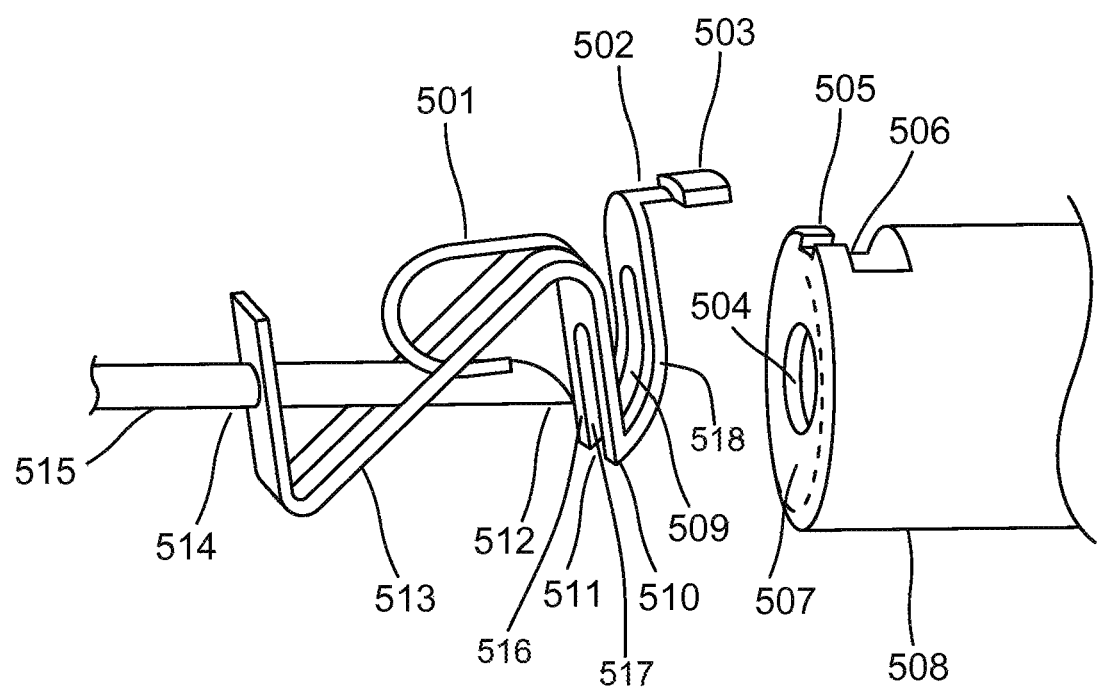
FIG. 5 illustrates a perspective view of a combination of an implementation of a clip and a needle tip showing a hub face.

FIG. 5 illustrates a perspective view of a combination of an implementation of a clip and a needle tip 512 in a detached state showing a hub face 507. The clip includes a spring arm 501, a clip narrow tab 502, and a clip broad tab 503. The hub aperture 504 enables passage of needle or cannula 515. The hub 508 also includes a hub narrow notch 505 and a hub broad notch 506. A distal part of the clip includes a first distal wall 516 defining a first distal aperture 517, a second distal wall 518 defining a clip third aperture 509, a bend of the third aperture 510, and a proximal part of the third aperture 511. The proximal part of the clip includes a second aperture 513 and a first clip aperture 514.

Figure 6:
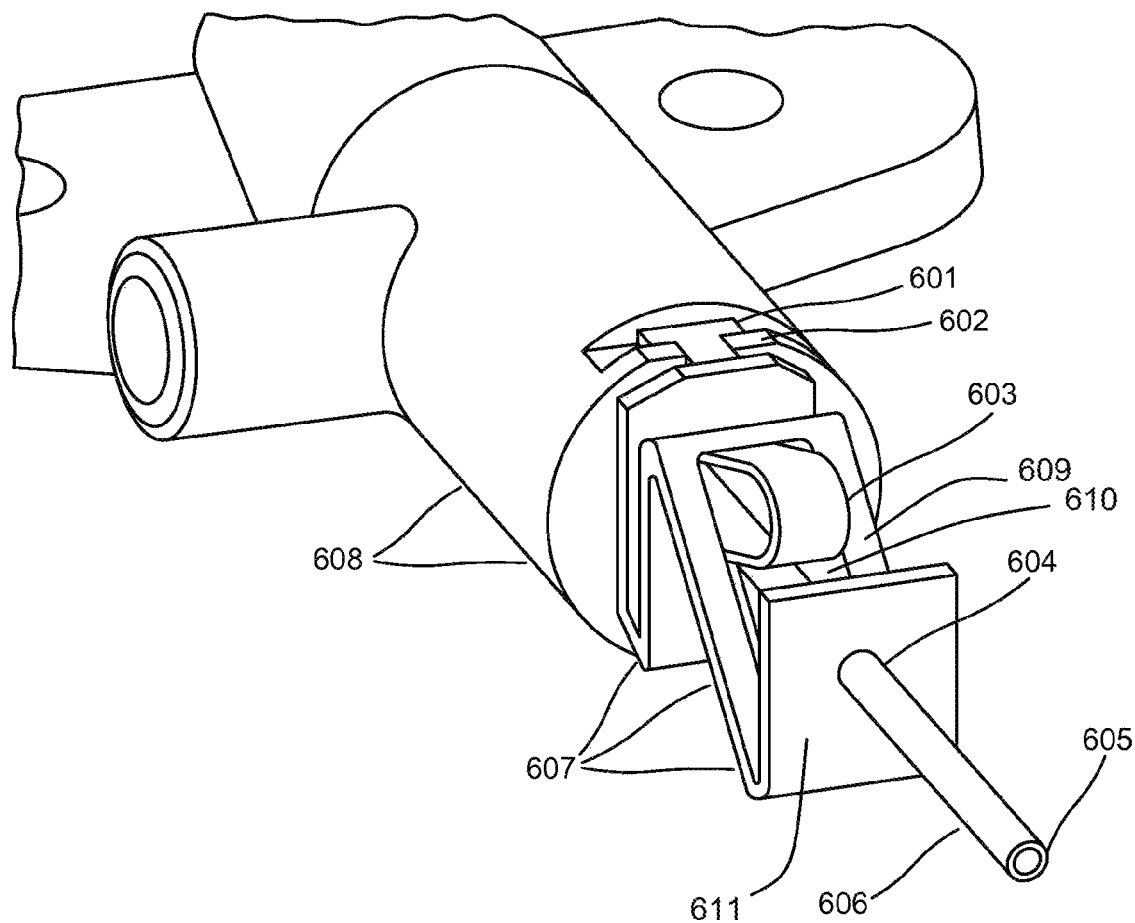
FIG. 6 illustrates an assembly of an implementation of a clip and a hub prior to assembly of the clip around a needle tip.

FIG. 6 illustrates a clip 607 and a hub 608 prior to assembly of the clip 607 around a needle tip of the needle 606. The hub 608 includes a hub broad notch 601 and a hub narrow notch 602. The hub broad notch 601 securely receives a clip broad tab and the hub narrow notch 602 securely receives a clip narrow tab. The secure receiving may be reversible, or alternatively, the removal of the tab from the notch can be permanent, such that the removed tab cannot be replaced securely in the corresponding notch. The clip 607 includes a spring arm 603, a first distal wall 609 defining a first distal aperture 610 and a second distal wall 611 defining a clip first aperture 604. A cross-section 605 of the needle 606 is also shown.

In some embodiments, the medical device does not comprise a safety clip contained entirely within a housing, within a shroud or cowl made of plastic, metal, or ceramic, within a hub, within a catheter, within a cannula, or within any housing.

FIG. 7 illustrates devices. In particular, FIG. 7A shows an aperture that contains a break, FIG. 7B shows a groove that contains a break, and FIG. 7C shows a tube that contains a break.

While the method and apparatus have been described in terms of what are presently considered to be the most practical and preferred embodiments, it is to be understood that the disclosure need not be limited to the disclosed embodiments. The disclosure is intended to cover various modifications and similar arrangements included within the spirit and scope of the claims, the scope of which should be accorded the broadest interpretation so as to encompass all such modifications and similar structures.

It should also be understood that a variety of changes may be made without departing from the essence of the invention. Such changes are also implicitly included in the description. Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these apparatuses and methods.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

What is claimed is:
1. A safety clip for a needle, the safety clip comprising:
   a proximal portion comprising a proximal wall, the proximal wall defining a proximal aperture for receiving a needle;
   a distal portion comprising a first distal wall directly connected to a second distal wall at a clip bend, the first distal wall defining a first distal aperture and the second distal wall defining a second distal aperture, the second distal wall being more distal than the first distal wall;
   a clip body extending from the proximal portion to the distal portion; and
   a spring arm located between the proximal portion and the distal portion, the spring arm being in contact with the needle, and the spring arm being configured to flex between a first conformation and a second conformation to move the safety clip relative to the needle, wherein:
   when a distal tip of the needle is distal of the second distal wall and the needle simultaneously extends through the proximal aperture, the first distal aperture and the second distal aperture, the spring arm is in the first conformation,
   when the distal tip of the needle is proximal of the second distal wall and distal of the first distal wall and the needle extends through the proximal aperture and the first distal aperture, the spring arm is in the second conformation, and
   the needle is closer to the clip bend connecting the first distal wall and the second distal wall within the first distal aperture when the spring arm is in the second conformation than when the spring arm is in the first conformation.

2. The safety clip of claim 1, further comprising a tab extending distally from the second distal wall, the tab being configured to be received within a tab placement portion in a hub of a medical device.

3. The safety clip of claim 2, wherein the tab comprises a proximal narrow region connected to a distal broad region.

4. The safety clip of claim 2, wherein:
   when the spring arm is in the first conformation, the tab is within the tab placement portion in the hub of the medical device, and
   when the spring arm is in the second conformation, the tab is outside of the tab placement portion in the hub of the medical device.

5. The safety clip of claim 2, wherein the medical device is a catheter, and the hub is a catheter hub.

6. The safety clip of claim 1, further comprising a tab receiving portion at the distal portion, the tab receiving portion being configured to receive a tab extending proximally from a hub of a medical device.

7. The safety clip of claim 1, wherein the first distal aperture is continuous with the second distal aperture.

8. The safety clip of claim 1, wherein the clip body defines a body aperture that receives the needle.

9. The safety clip of claim 1, wherein:
when the spring arm is in the first conformation, the spring arm exerts a first force on the needle, and
when the spring arm is in the second conformation, the spring arm exerts a second force on the needle, the second force being less than the first force.

10. The safety clip of claim 1, wherein when the spring arm is in the second conformation, the spring arm is extended relative to when the spring arm is in the first conformation.

11. The safety clip of claim 1, wherein:
the proximal aperture is configured to allow sliding of the safety clip relative to the needle in the first conformation, and
the proximal aperture is configured to prevent sliding of the safety clip relative to the needle in the second conformation.

12. The safety clip of claim 1, wherein the proximal aperture comprises sharp internal edges.

13. The safety clip of claim 1, wherein:
the proximal portion, the distal portion, and the clip body are made of a first material, and the spring arm is made of a second material that is different from the first material.

14. The safety clip of claim 13, wherein the second material is a metal.

15. The safety clip of claim 1, wherein the spring arm is connected to the safety clip at a location proximal to the distal portion.

16. The safety clip of claim 1, wherein the safety clip is not enclosed within a housing.

17. The safety clip of claim 1, wherein a distal face of the second distal wall and a proximal face of a hub of a medical device have a mating geometry.

18. The safety clip of claim 1, wherein, when the spring arm is in the first conformation, the proximal wall and the first distal wall are parallel to one another.

19. The safety clip of claim 1, wherein the spring arm extends from the clip body.

20. The safety clip of claim 1, wherein at least part of the first distal aperture and at least part of the second distal aperture overlap in a direction perpendicular to a longitudinal axis of the needle.

21. The safety clip of claim 1, wherein the needle is closer to the clip bend connecting the first distal wall and the second distal wall in an axis transverse to the longitudinal axis of the needle within the first distal aperture when the spring arm is in the second conformation than when the spring arm is in the first conformation.

* * * * *